United States Patent
Malviya et al.

(10) Patent No.: US 12,124,489 B2
(45) Date of Patent: Oct. 22, 2024

(54) SYSTEM AND METHOD FOR EXAMINING RELEVANCY OF DOCUMENTS

(71) Applicant: L&T TECHNOLOGY SERVICES LIMITED, Chennai (IN)

(72) Inventors: Ankit Malviya, Betul (IN); Madhusudan Singh, Bangalore (IN); Mridul Balaraman, Bangalore (IN); Prakhar Srivastava, Prayagraj (IN)

(73) Assignee: L&T TECHNOLOGY SERVICES LIMITED, Chennai (IN)

( * ) Notice: Subject to any disclaimer, the term of this patent is extended or adjusted under 35 U.S.C. 154(b) by 0 days.

(21) Appl. No.: 18/104,930

(22) Filed: Feb. 2, 2023

(65) Prior Publication Data
US 2023/0185835 A1     Jun. 15, 2023

(51) Int. Cl.
*G06F 16/00*     (2019.01)
*G06F 16/33*     (2019.01)

(52) U.S. Cl.
CPC ............... *G06F 16/3344* (2019.01)

(58) Field of Classification Search
CPC .................................... G06F 16/3344
USPC ........................................ 707/728
See application file for complete search history.

(56) References Cited

U.S. PATENT DOCUMENTS

| | | | | |
|---|---|---|---|---|
| 6,363,378 B1 * | 3/2002 | Conklin | ............ | G06F 16/3325 |
| | | | | 707/999.005 |
| 9,449,080 B1 * | 9/2016 | Zhang | ............... | G06F 16/3346 |
| 10,606,903 B2 * | 3/2020 | Narayanam | .......... | G06F 16/248 |
| 2019/0286898 A1 * | 9/2019 | Powell | ................. | G06F 16/22 |
| 2020/0226143 A1 * | 7/2020 | Miller | .............. | G06F 16/24578 |

FOREIGN PATENT DOCUMENTS

KR     20110027729 A *   3/2011   .............. G06N 7/01

* cited by examiner

*Primary Examiner* — Monica M Pyo
(74) *Attorney, Agent, or Firm* — Kendal M. Sheets

(57) ABSTRACT

Disclosed herein is system and method for examining relevancy of documents. The system, based on request from the user extracts documents from one or more data sources. The system then obtains from the user, user intention information and user queries. The system then analyses each document with respect to user intention information in order to determine a relevancy level of each document. The relevancy level is indicated in the form of a ranking score. The system ranks and displays the documents to the user in the order of their scores. The system also highlights important excerpts from the documents and provides one or more responses to the one or more user queries submitted by the user for each and every document. Based on the received responses, user provides feedback for further training the system, thereby achieving better accuracy.

13 Claims, 9 Drawing Sheets

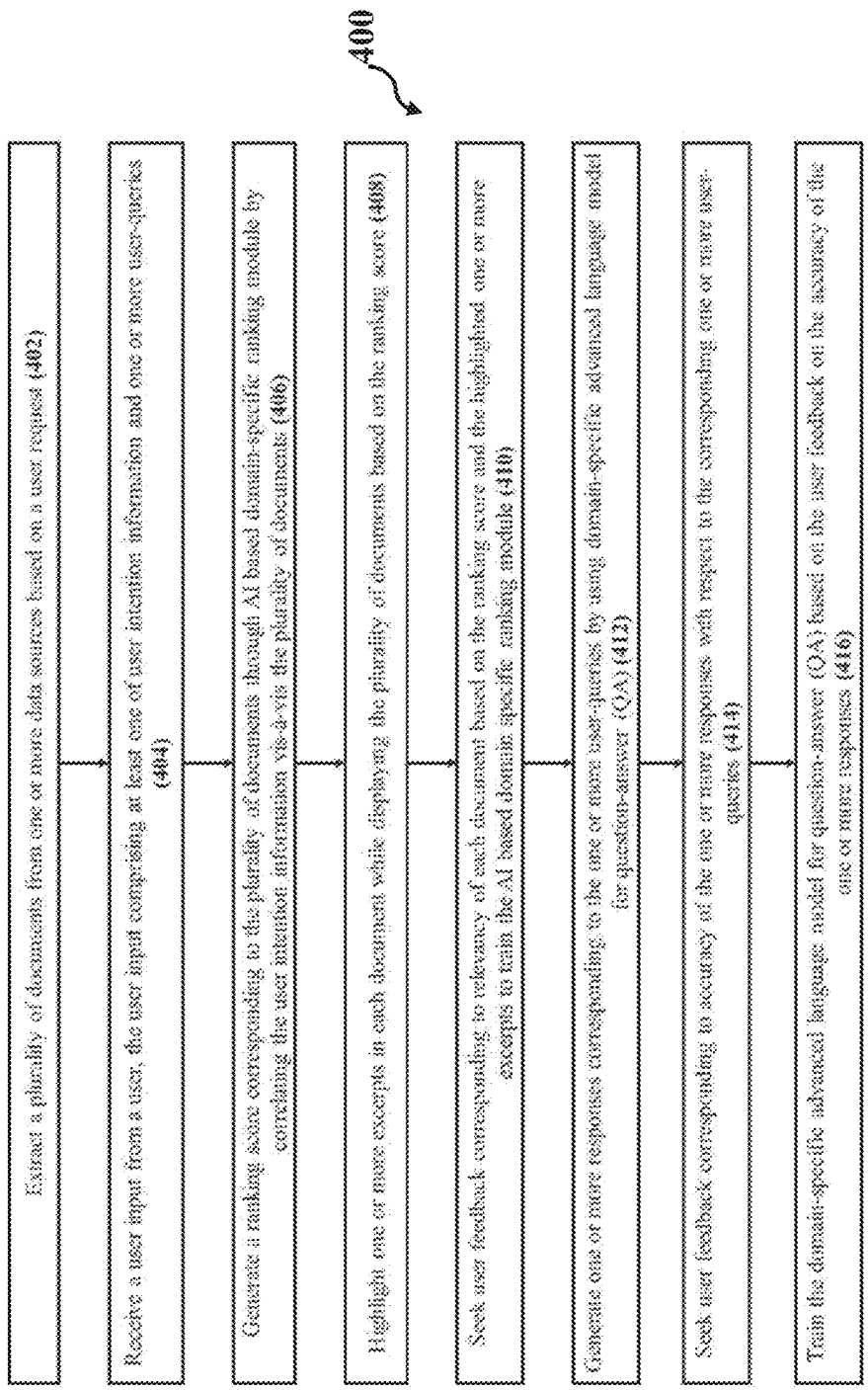

SYSTEM AND METHOD FOR EXAMINING RELEVANCY OF DOCUMENTS

TECHNICAL FIELD

The present disclosure relates to a field of data analysis. More particularly, it relates to analyzing documents extracted from various sources so as to examine the relevancy of the documents.

BACKGROUND

The following description includes information that may be useful in understanding the present disclosure. It is not an admission that any of the information provided herein is prior art or relevant to the present claims, or that any publication specifically or implicitly referenced is prior art.

Creating a report for a research-based study requires extracting and analysing a large number of documents manually and is therefore a highly tedious task. An individual has to spend long time in finding relevant documents, and post finding the relevant documents, has to study each and every document to decide whether to include the document in the study or not. For instance, an individual wants to prepare a clinical evaluation report (CER) describing clinical evaluation of a medical device. For this purpose, the individual has to first identify clinical data from existing literature, clinical experience, clinical trials, or any combination of the three. The individual has to then appraise the data's relevance, applicability, quality, and significance and eventually articulate their conclusions in the CER, based on the data collected. Further, since these two steps are crucial for the quality of the generated report, these steps must be performed meticulously. Therefore, the whole process becomes highly time consuming and mentally exhausting when performed manually.

There is therefore a need for a method and a system that reduces the manual effort involved in identification and appraisal of data and examining relevancy of documents.

SUMMARY

The present disclosure overcomes one or more shortcomings of the prior art and provides additional advantages discussed throughout the present disclosure. Additional features and advantages are realized through the techniques of the present disclosure. Other embodiments and aspects of the disclosure are described in detail herein and are considered a part of the claimed disclosure.

In one non-limiting embodiment of the present disclosure, a method for examining relevancy of documents is disclosed. The method comprises extracting a plurality of documents from one or more data sources based on a user request. The method further comprises receiving a user input from a user, the user input comprising at least one of user intention information and one or more user-queries. The method further comprises generating a ranking score for each of the plurality of documents through domain specific ranking module by correlating the user intention information vis-à-vis the plurality of documents, wherein the ranking score indicates a relevancy level of each of the plurality of documents with respect to the user intention information. The method further comprises highlighting one or more excerpts in each document while displaying the plurality of documents based on the ranking score. The method further comprises seeking user feedback corresponding to relevancy of each document based on the ranking score and the highlighted one or more excerpts to train the domain specific ranking module.

In yet another non-limiting embodiment of the present disclosure, a system for examining relevancy of documents is disclosed. The system comprises an extraction unit configured to extract a plurality of documents from one or more data sources based on a user request. The system further comprises a receiving unit configured to receive a user input from a user, the user input comprising at least one of user intention information and one or more user-queries. The system further comprises a score generation unit configured to generate a ranking score corresponding to the plurality of documents through domain specific ranking module by correlating the user intention information vis-à-vis the plurality of documents, wherein each ranking score indicates relevancy level of a document with respect to the user intention information. The system further comprises a highlighting unit configured to highlight one or more excerpts in each document while displaying the plurality of documents based on the ranking score. The system further comprises a feedback unit configured to seek user feedback corresponding to relevancy of each document based on the ranking score and the highlighted one or more excerpts. The system further comprises a training unit configured to train the domain specific ranking module based on the user feedback.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF DRAWINGS

The embodiments of the disclosure itself, as well as a preferred mode of use, further objectives and advantages thereof, will best be understood by reference to the following detailed description of an illustrative embodiment when read in conjunction with the accompanying drawings. One or more embodiments are now described, by way of example only, with reference to the accompanying drawings in which:

FIG. 4 illustrates a flowchart of a method for examining relevancy of documents, in accordance with an embodiment of the present disclosure.

Figure 1A:
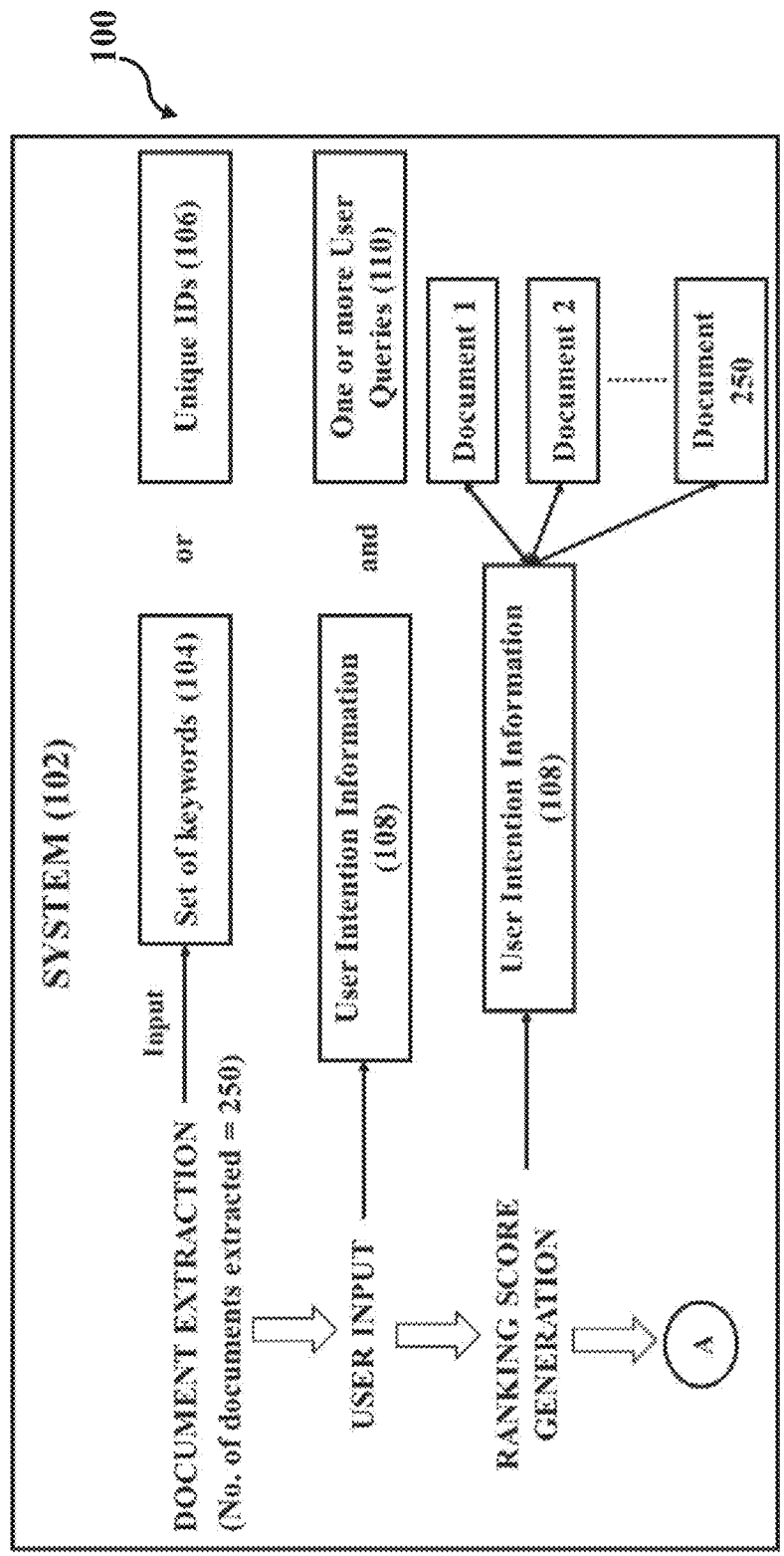
FIGS. 1A-1C illustrates an environment of a system for examining relevancy of documents, in accordance with an embodiment of the present disclosure.

The figures depict embodiments of the disclosure for purposes of illustration only. One skilled in the art will readily recognize from the following description that alternative embodiments of the structures and methods illustrated herein may be employed without departing from the principles of the disclosure described herein.

DETAILED DESCRIPTION

The foregoing has broadly outlined the features and technical advantages of the present disclosure in order that the detailed description of the disclosure that follows may be better understood. It should be appreciated by those skilled in the art that the conception and specific embodiment disclosed may be readily utilized as a basis for modifying or designing other structures for carrying out the same purposes of the present disclosure.

The novel features which are believed to be characteristic of the disclosure, both as to its organization and method of operation, together with further objects and advantages will be better understood from the following description when considered in connection with the accompanying Figures. It is to be expressly understood, however, that each of the Figures is provided for the purpose of illustration and description only and is not intended as a definition of the limits of the present disclosure.

Disclosed herein is a system and method for examining relevancy of documents. The task of creating a research report, for instance, an evaluation report, a literature survey report, a qualitative report and a quantitative report, is a highly tedious and time-consuming task. An individual has to spend a long time to collect data that is relevant to his study. Post that, the individual has to analyze the collected data to examine data's relevance, applicability, quality, and significance. However, the first step of collecting the data and the subsequent step of analysing the data is highly tedious and may often take days to complete when undertaken manually. Since the tasks of collecting the data and analysing the data are very crucial with respect to the quality of the generated report, it becomes imperative that these tasks are performed meticulously. There is always a room for improvement since it is not humanly possible for an individual to analyze each and every document meticulously when performing the task manually.

The present disclosure provides a system that assists a user in the tasks of collecting and analysing the documents. The system, based on a request from the user, extracts documents from the data sources. The extracted documents are broadly based on the search that the user wants to conduct. The system then receives a user's intention behind performing the study along with certain queries that the user wishes to be answered by the system with respect to the extracted documents. The queries are domain-specific and can be customized by the user based on his/her needs and based on the domain of the study. For instance, a user who is working in a bio-medical domain would have different queries in comparison to a user who is working in a nanomaterials domain or transportation domain. The system then analyses each document with respect to user's intention to determine a relevancy level of each document. The relevancy level may be indicated in the form of a ranking score. The system ranks and displays the documents to the user in the order of their ranking scores. This allows the user to be view the documents in the order of relevancy. Further, the system also highlights important excerpts from the documents to help user to focus only on the highlighted excerpts instead of reading the entire document. Furthermore, the system also provides responses to the queries submitted by the user for each and every document. In this manner, it becomes comparatively easier for the user to decide whether to include or exclude a document from his study. The time taken to arrive at such a decision is greatly reduced as the user doesn't have to study the entire document for examining its relevancy. The detailed working and explanation of the system is described in the subsequent paragraphs.

Figure 1B:
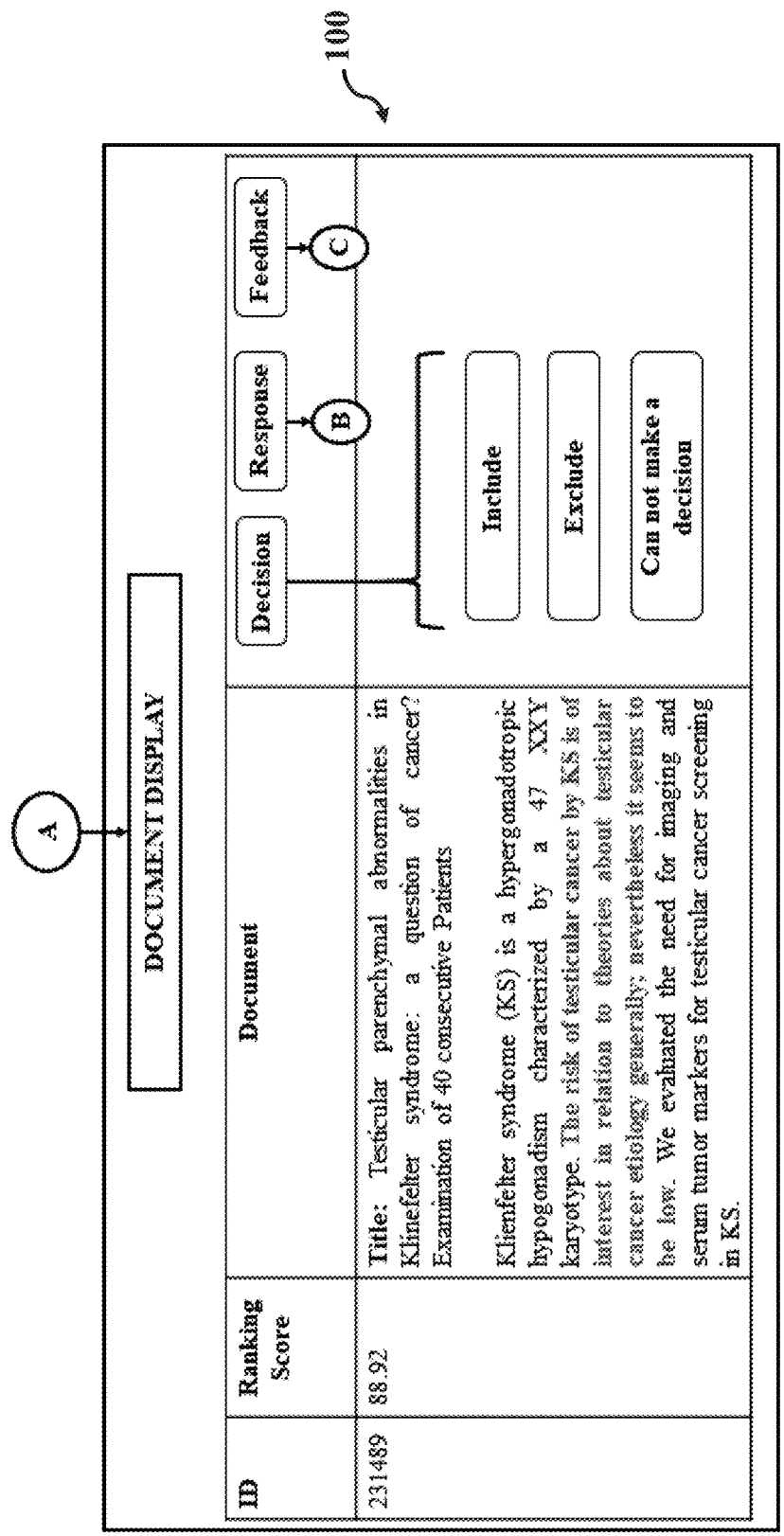
Figure 1C:
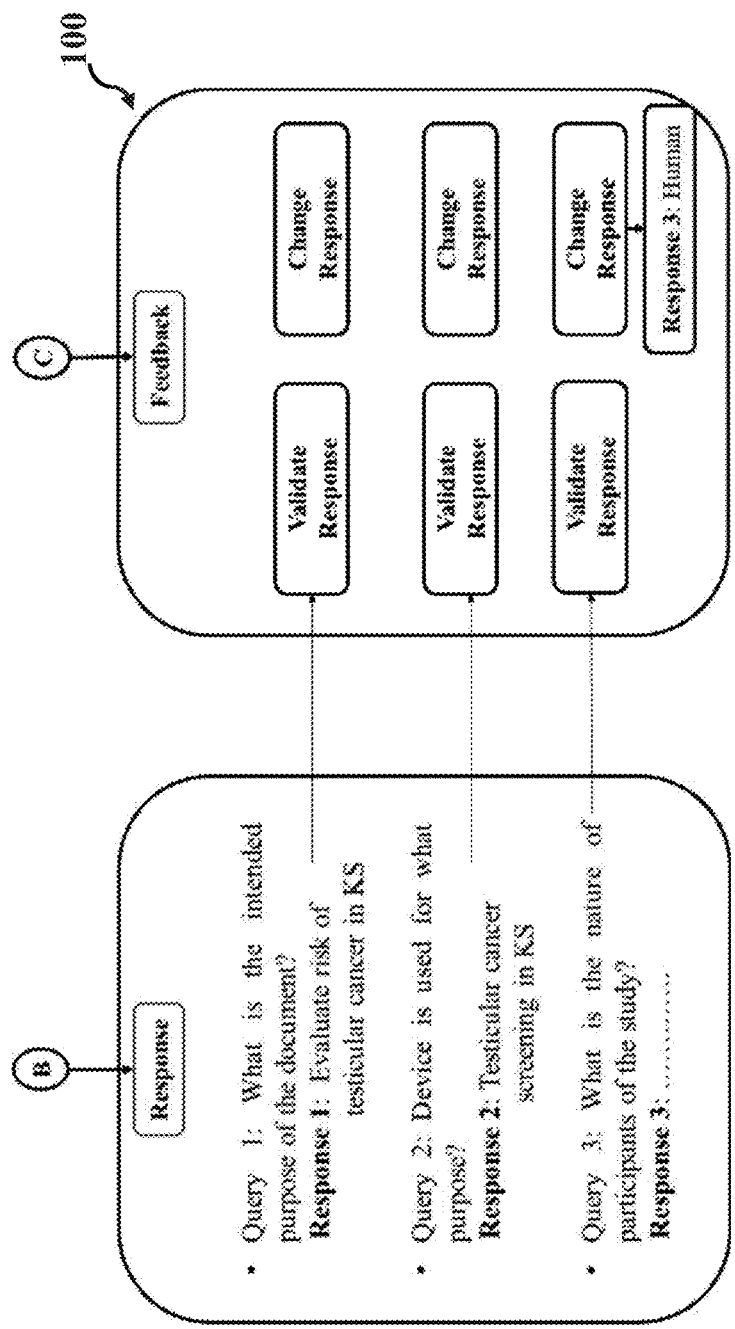

FIG. 1A-1C show an exemplary environment 100 of a system for examining relevancy of documents, in accordance with an embodiment of the present disclosure. It must be noted by a skilled person that the exemplary environment 100 of FIG. 1A is explained considering that a user wants to create a clinical evaluation report (CER) in the bio-medical domain. A person skilled in the art may further understand that the system 102 may also be implemented in various environments, other than as shown in FIG. 1A.

Figure 2:
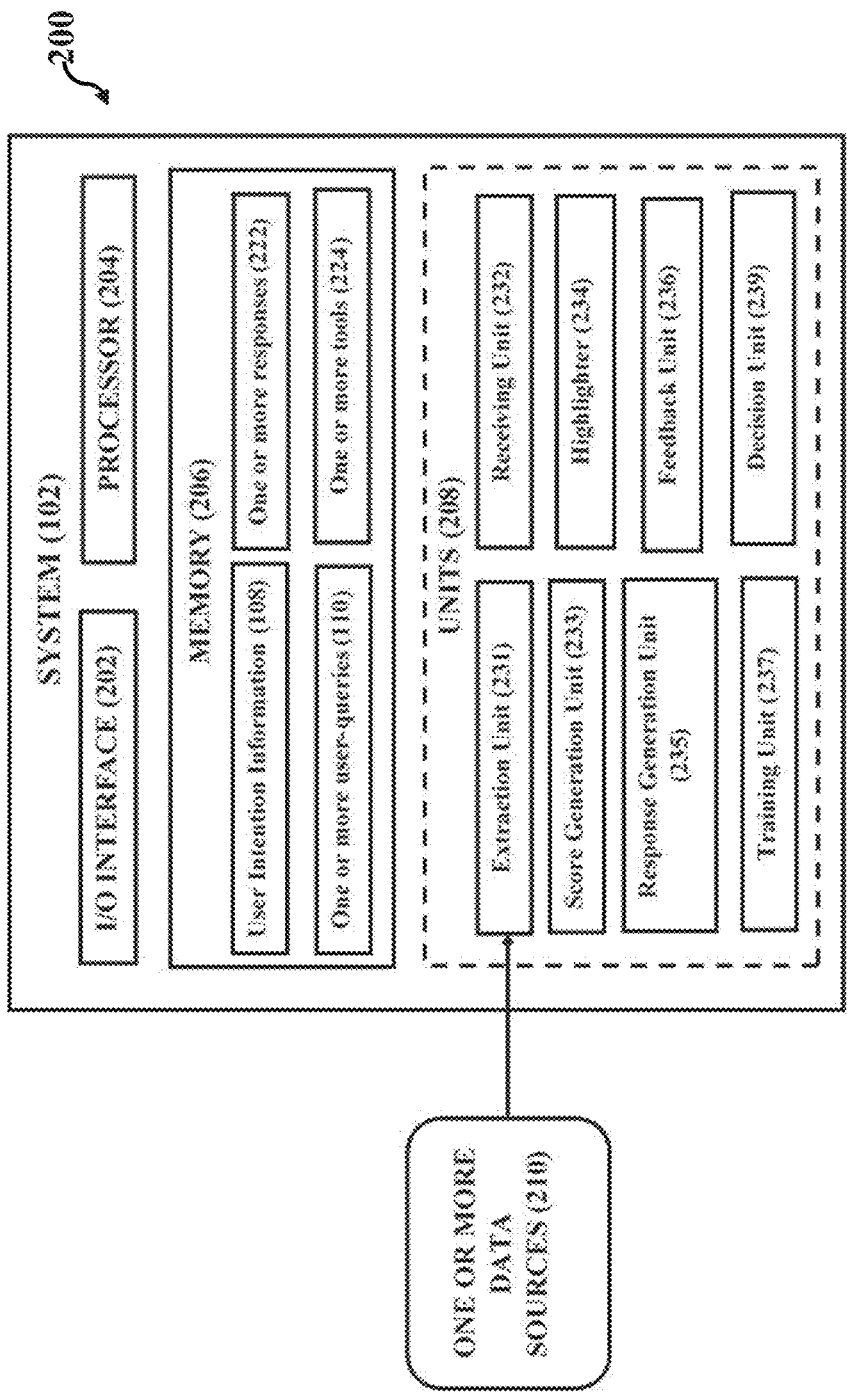
FIG. 2 illustrates a block diagram of the system for examining relevancy of documents, in accordance with an embodiment of the present disclosure.

The exemplary environment 100 is explained in conjunction with FIG. 2 that shows a block diagram 200 of a system 102, in accordance with an embodiment of the present disclosure. Although the present disclosure is explained considering that the system 102 is implemented on a server, it may be understood that the system 102 may be implemented as a tool in a variety of computing systems, such as a laptop computer, a desktop computer, a notebook, a workstation, a mainframe computer, a server, a network server, a cloud-based computing environment.

In one implementation, the system 102 may comprise an I/O interface 202, a processor 204, a memory 206 and the units 208. The memory 206 may be communicatively coupled to the processor 204 and the units 208. Further, the memory 208 may store user intention information 108, one or more queries 110, one or more responses 222 and one or more tools 224. The significance and use of each of the stored quantities is explained in the subsequent paragraphs. The processor 204 may be implemented as one or more microprocessors, microcomputers, microcontrollers, digital signal processors, central processing units, state machines, logic circuitries, and/or any devices that manipulate signals based on operational instructions. Among other capabilities, the processor 204 is configured to fetch and execute computer-readable instructions stored in the memory 206. The I/O interface 202 may include a variety of software and hardware interfaces, for example, a web interface, a graphical user interface, and the like. The I/O interface 202 may enable the system 102 to communicate with other computing devices, such as web servers and external data servers (not shown). The I/O interface 202 may facilitate multiple communications within a wide variety of networks and protocol types, including wired networks, for example, LAN, cable, etc., and wireless networks, such as WLAN, cellular, or satellite. The I/O interface 202 may include one or more ports for connecting many devices to one another or to another server.

In one implementation, the units 208 may comprise an extraction unit 231, a receiving unit 232, a score generation unit 233, a highlighting unit 234, a response generation unit 235, a feedback unit 236, a training unit 237, and a decision unit 238. According to embodiments of the present disclosure, these units 231-238 may comprise hardware components like processor, microprocessor, microcontrollers, application-specific integrated circuit for performing various operations of the system 102. It must be understood that the processor 204 may perform all the functions of the units 231-238 according to various embodiments of the present disclosure.

Referring to FIG. 1A, the environment 100 shows the system 102 that extracts a plurality of documents from one or more data sources 210 based on a user request. In accordance with FIG. 2, the extraction of documents is performed by the extraction unit 231. In one embodiment, the user request comprises a set of keywords 104 pertaining to the plurality of documents. For instance, if the subject-matter of the CER that the user wants to create the report related to "quantitative determination of Access alpha-feto-protein (AFP) in human serum as an aid to manage patients with non-seminomatous testicular cancer", the user provides a set of keywords 104 that may comprise "AFP", "human", "testicular cancer". The extraction unit 231 based on the set of keywords extracts the plurality of documents. In another embodiment, the user request comprises the user providing a plurality of unique IDs 106 pertaining to the plurality of documents. The plurality of unique IDs are provided to the extraction unit 231 that extracts the plurality of documents corresponding to the plurality of unique IDs 106. In accordance with the exemplary environment 100 depicted in FIG. 1A, the plurality of documents extracted is 250.

Once the plurality of documents are extracted, the receiving unit 232 receives a user input. In one embodiment, the user input comprises user intention information 108 indicating using natural language, an intention behind creating said CER. In accordance with the exemplary environment 100, the user intention information 110 may read like: "The Access alpha-fetoprotein (AFP) assay is a paramagnetic particle, chemiluminescent immunoassay for use with the Access Immunoassay Systems for the quantitative determination of AFP in Human-serum as an aid in management of patients with non-seminomatous testicular cancer. Maternal serum and amniotic fluid to aid in detection of fetal Open Neural Tube Defects (ONTD)". The user input further comprises one or more user queries 110 pertaining to the plurality of documents as shown in FIG. 1A and FIG. 1C. For instance, the one or more user queries 110 may comprise questions such as "What is the intent of the document?", "What is the device used for?", "What is the nature of participants of the study?" etc. It must be noted by a skilled person that the one or more user queries 110 are customizable based on the needs of the user. That is, the one or more user queries 110 can be edited or drafted based on the kind of study the user is undertaking and the domain the study belongs to. For instance, according to an exemplary environment 100 the study is of bio-medical domain, the one or more queries 110 are relevant to the bio-medical domain. However, a user whose study is in the domain of nano-materials may have different set of queries than mentioned above and can customize the queries based on his needs.

To examine the relevancy of the plurality of documents with respect to the user intention information 108, the score generation unit 233 correlates user intention information 108 vis-à-vis the plurality of documents to generate a ranking score for each document. The ranking score indicates relevancy level of each document with respect to user intention information 108. In accordance with the exemplary environment 100, depicted in FIG. 1A, the user intention information 108 is correlated vis-à-vis each of the 250 extracted documents.

Figure 3:
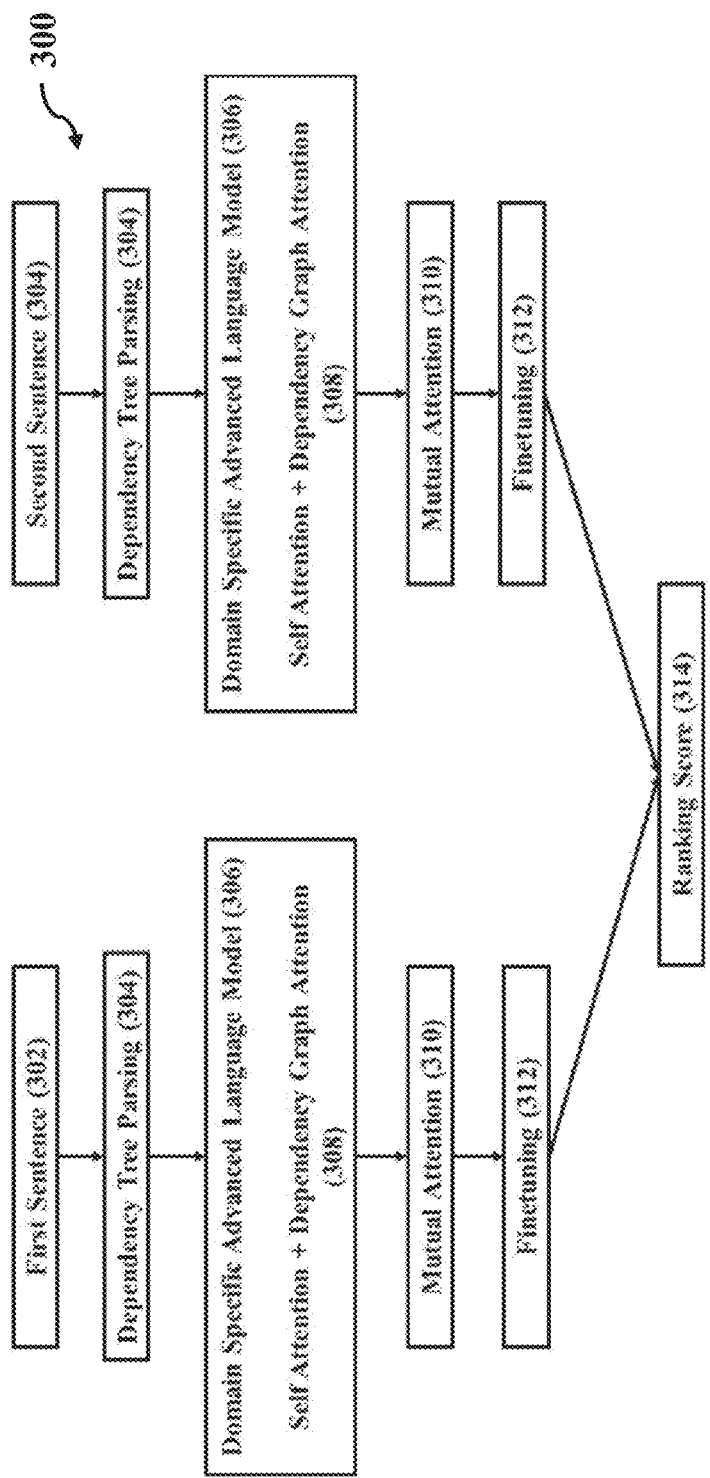
FIG. 3 illustrates an exemplary embodiment illustrating a domain specific ranking module, in accordance with an embodiment of the present disclosure.

To correlate the user intention information 108 vis-à-vis the plurality of documents, the score generation unit 233 employs a domain specific ranking module 300 as illustrated in FIG. 3. The domain specific ranking module 300 is stored in the memory 206 as one of the one or more tools 224. The details of the domain specific ranking module 300 is explained with the help of an example in the subsequent paragraphs.

At step 302 of the domain specific ranking module 300, a sentence pair is input. The sentence pair comprises a first sentence derived from user intention information 110 and a second sentence derived from one of the plurality of documents. For instance, the sentence pair may comprise—

First Sentence—AFP is detected in patients with NSTC; and

Second Sentence—Elevated AFP revealed mixed germ cell tumours.

Figures 3A, 3B:
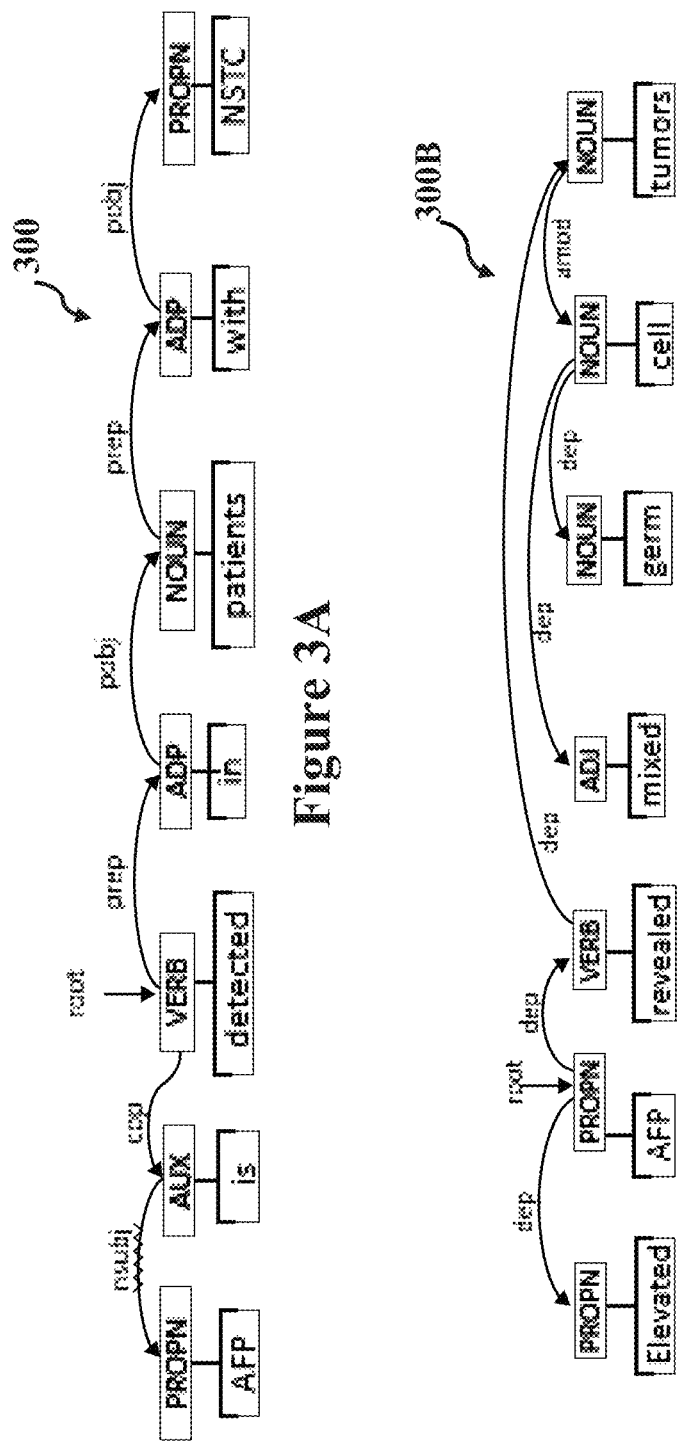
FIGS. 3A and 3B illustrate the dependency trees and corresponding to a first sentence and a second sentence, in accordance with an embodiment of the present disclosure.

At step 304 of the domain specific ranking module 300, a first dependency tree 300A corresponding to the first sentence and a second dependency tree 300B corresponding to the second sentence is generated. The first and the second dependency trees 300A, 300B represent grammatical structure of the first sentence and the second sentence to uncover their syntactic structure as illustrated in FIGS. 3A and 3B.

At step 306 of the domain specific ranking module 300, a domain specific advanced language model is employed to encode a first set of tokens (or words) corresponding to the first sentence and a second set of tokens (or words) corresponding to the second sentence in domain-specific manner so as to not alter a meaning of the first sentence and the second sentence. The working of the domain-specific advanced language model for the first sentence and the second sentence is illustrated in tables 1 and 2, respectively.

TABLE 1

Domain Specific Transformation for first sentence

| First Sentence | AFP | Is | detected | In | Patients | With | NSTC | . |
|---|---|---|---|---|---|---|---|---|
| Tokens | 'afp' | 'is' | 'detected' | 'in' | 'patients' | 'with' | 'nstc' | '.' |
| Encoding | 28634 | 165 | 2490 | 121 | 568 | 190 | 3281205 | |

TABLE 2

Domain Specific Transformation for second sentence

| First Sentence | Elevated | AFP | Revealed | Mixed | Germ | Cell | tumours | . |
|---|---|---|---|---|---|---|---|---|
| Tokens | 'elevated' | 'afp' | 'revealed' | 'mixed' | 'germ' | 'cell' | 'tumours' | '.' |
| Encoding | 5161 | 28634 | 2861 | 4055 | 2927 | 377 | 11571 | 205 |

However, if instead of domain-specific advanced language model, a normal language model is used, the tokens of the first sentence would be generated as— ['a', '##f' '##p', 'is', 'detected', 'in', 'patients', 'with', 'n', '##s', '##t', '##c', '.'"] and the tokens of the second sentence would be generated as—['elevated', 'a', '##f', '##p', 'revealed', 'mixed', 'ge', '##rm', 'cell', 'tu', '##mour', '##s', '.']. Hence, the meaning of the first and the second sentence would be lost.

Figure 3C:
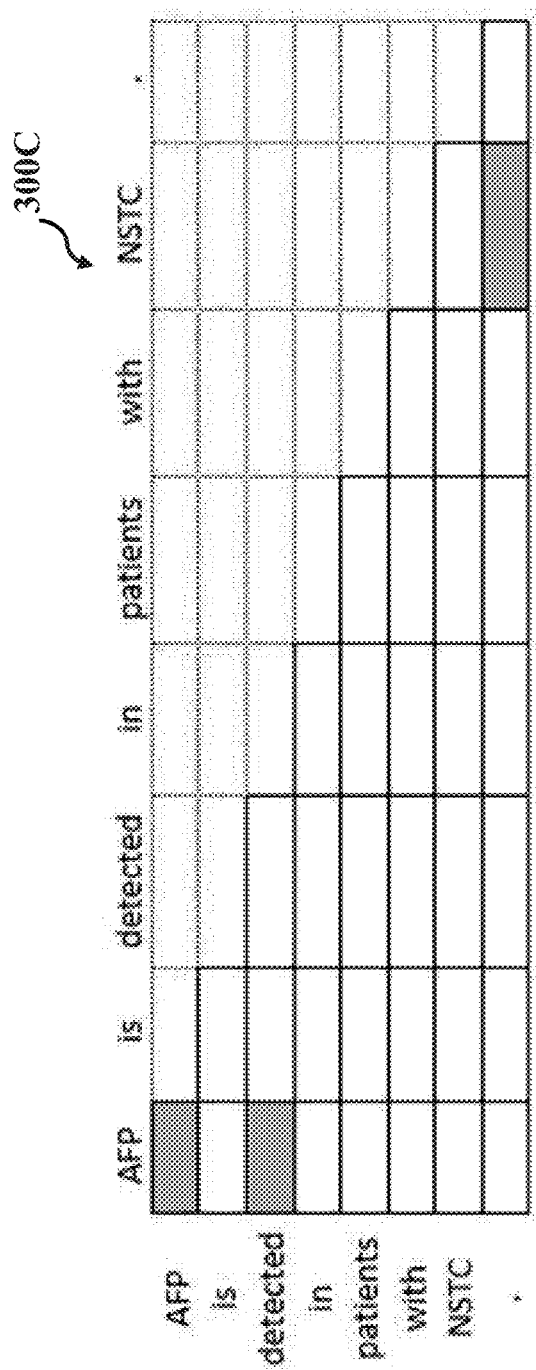
FIGS. 3C and 3D illustrates attention matrices and corresponding to a first sentence and a second sentence respectively, in accordance with an embodiment of the present disclosure.
Figure 3D:
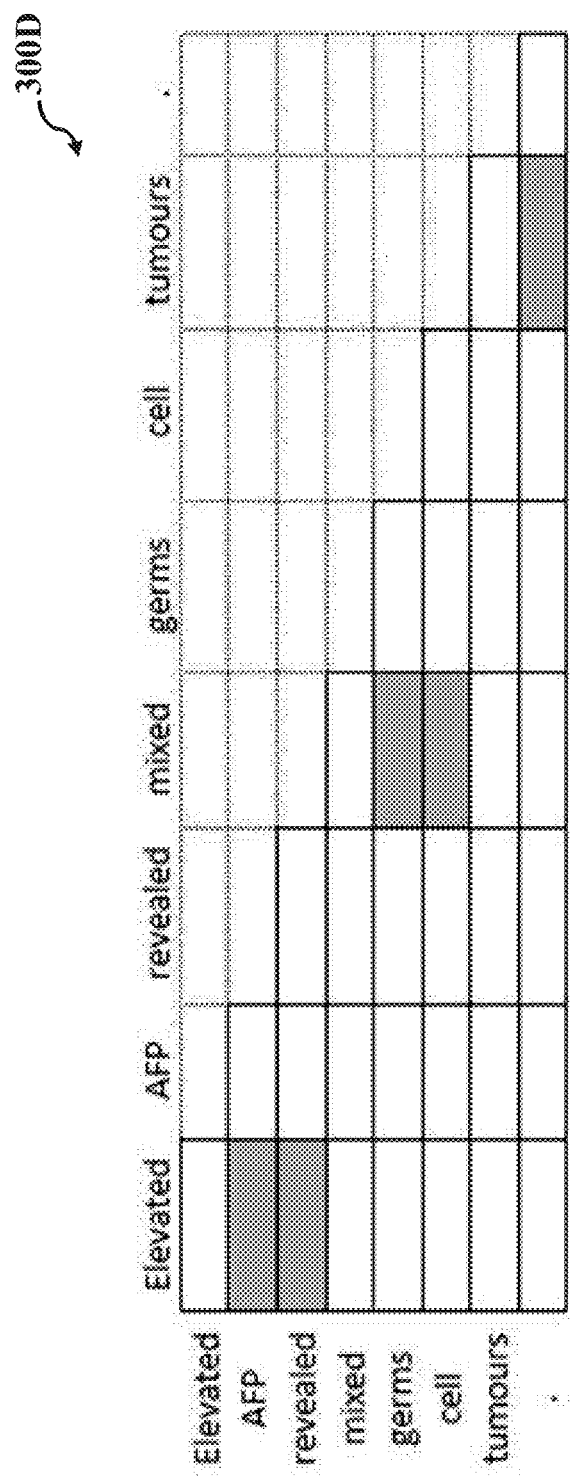

At step 308 of the domain specific ranking module 300, a first attention matrix corresponding to the set of words of the first sentence and a second attention matrix corresponding to the set of words of the second sentence is created to establish explicit dependency relationship between the set of words of the first sentence and the set of words of the second sentence. The attention matrices corresponding to the set of words of first sentence and the set of words of the second sentence is depicted in FIGS. 3C and 3D respectively, where the highlighted cells are with respect to the attention weights.

At step 310 of the domain specific ranking module 300, mutual attention technique is employed to generate semantic representations corresponding to the first sentence and the second sentence. Mutual attention takes into consideration synonyms and near-synonyms of a word at different positions such that the similarity between words does not go unnoticed due to the positioning of words or due to the use of synonyms or near-synonyms. For instance, the first sentence "AFP is detected in patients with NSTC" can also be expressed as "NSTC patients are detected with AFP levels" and the second sentence "Elevated AFP revealed mixed germ cell tumours" can also be expressed as "Mixed germ cell tumours are detected with high AFP".

At step 312 of the domain specific ranking module 300, the set of words of the first sentence and the set of words of the second sentence are finetuned to generate semantically meaningful sentence representations or embeddings. The finetuning is accomplished by providing the set of words of the first sentence and the second sentence to a dual branch network with shared parameters to minimize a loss function. This dual branch network with shared parameters is pretrained to minimize the loss function by providing the model with pairs of similarity-feedback-labelled sentences and minimizing the loss between the semantic representations of the sentences.

At step 314 of the domain specific ranking module 300, ranking score is generated for the finetuned first sentence and the second sentence by employing a similarity measurement technique such as cosine similarity, Manhattan distance similarity, Euclidean distance similarity etc. It may however be noted by a skilled person that the similarity measurement techniques other than the ones mentioned above may also be used.

The procedure described in steps 302-314 is iteratively carried out to determine a ranking score for each of the plurality of documents in accordance with the user intention information 108.

Once the ranking score for the plurality of documents is generated, the plurality of documents are displayed in order of their ranking scores as depicted in FIG. 1B. In one embodiment, the document with highest ranking score may be displayed at the top. However, in another embodiment, the document with highest ranking score may be displayed at the bottom. Further, as shown in FIG. 1B, each document is displayed with its unique ID and its ranking score. It may be noted by a skilled person that the ranking score depicted in FIG. 1B is out of 100, however, the ranking score can be generated or represented in other forms.

Further, for each displayed document, the highlighting unit 234 highlights one or more excerpts that are important in view of the user intention information 108. It may be understood by a skilled person that one or more excerpts may comprise one or more paragraphs and/or one or more sentences. To highlight one or more important paragraphs, the domain specific ranking module 300 is employed by the highlighting unit 234 to identify a paragraph in a document with highest relevancy to the user intention information 108. Further, to highlight one or more important sentences in an important paragraph, attention weights of respective tokens (or words) of the sentences of the important paragraph and the user intention information 108 are calculated by the score generation unit 233. Based on the attention weights, each token is assigned a score. Based on the scores, a start and an end of the important part of the most relevant paragraph is obtained which is highlighted as an important sentence by the highlighting unit 234.

Highlighting of the one or more excerpts allows the user to readily identify the sections of a document that are most relevant to his/her intended purpose as defined by him/her in the user intention information 108.

Further, as shown in FIG. 1C, the system 102 allows a user to view one or more responses to the one or more user queries 110 provided by him/her by selecting a Response tab as shown in. The responses to the one or more user queries 110 is provided in FIG. 1B by a response generation unit 235 that employs a domain specific advanced language model for question-answers (QA) stored as one or more tools 224 in the memory 206 of the system 102. The generated one or more responses 222 are stored in the memory 206. Further, based on the generated one or more responses, the feedback unit 236 allows the user to provide a feedback to the one or more responses. For instance, as shown in exemplary environment 100 of FIG. 1A, the user is provided with an option to validate the response provided by the response generation unit 235 or change the response if he/she is not satisfied with the response provided or if the response generation unit was incapable of providing a response. Based on the feedback, the training unit 237, re-trains the advanced language model for question-answer (QA).

The system 102 further enables the user to select one or more relevant documents by providing a decision tab as shown in FIG. 1A. The decision tab is controlled by the decision unit 238 and provides options to the user to either "Include" or "Exclude" a particular document. However, if the user is not able to decide, the decision unit 238 allows the user to revisit a particular document by providing "Cannot make a decision" option to the user.

Therefore, the system 102 through the interaction of its various components, makes it easier for the viewer to identify relevant documents with minimal time and effort, thereby enhancing user's experience. Further, the manner in which the ranking score for each of the plurality of documents is generated is highly extensive and accurate since the domain specific ranking module 300 employs a combination of various techniques.

FIG. 4 depicts a method 400 for examining relevancy of a plurality of documents, in accordance with an embodiment of the present disclosure.

As illustrated in FIG. 4, the method 400 includes one or more blocks illustrating a method for managing information in the manufacturing plant. The method 400 may be described in the general context of computer executable instructions. Generally, computer executable instructions may include routines, programs, objects, components, data structures, procedures, modules, and functions, which perform specific functions or implement specific abstract data types.

The order in which the method 400 is described is not intended to be construed as a limitation, and any number of the described method blocks may be combined in any order to implement the method. Additionally, individual blocks may be deleted from the methods without departing from the spirit and scope of the subject matter described.

At block 402, the method 400 may include extracting a plurality of documents from one or more data sources 210 based on a user request.

At block 404, the method 400 may include receiving a user input from a user, the user input comprising at least one of user intention information 108 and one or more user-queries 110.

At block 406, the method 400 may include generating a ranking score for each of the plurality of documents by correlating the user intention information 108 vis-à-vis the plurality of documents.

At block 408, the method 400 may include highlighting one or more excerpts in each document while displaying the plurality of documents based on the ranking score.

At block 410, the method 400 may include seeking user feedback corresponding to relevancy of each document based on the ranking score and the highlighted one or more excerpts to train the domain specific ranking module.

At block 412, the method 400 may include generating one or more responses 222 corresponding to the one or more user-queries 110 by using domain-specific advanced language model for question-answer (QA).

At block 414, the method 400 may include seeking user feedback corresponding to accuracy of the one or more responses 222 with respect to the corresponding one or more user-queries 110.

At block 416, the method 400 may include training the domain-specific advanced language model for question-answer (QA) based on the user feedback on the accuracy of the one or more responses 222.

A description of an embodiment with several components in communication with each other does not imply that all such components are required. On the contrary, a variety of optional components are described to illustrate the wide variety of possible embodiments of the disclosure.

When a single device or article is described herein, it will be clear that more than one device/article (whether they cooperate) may be used in place of a single device/article. Similarly, where more than one device or article is described herein (whether they cooperate), it will be clear that a single device/article may be used in place of the more than one device or article or a different number of devices/articles may be used instead of the shown number of devices or programs. The functionality and/or the features of a device may be alternatively embodied by one or more other devices which are not explicitly described as having such functionality/features. Thus, other embodiments of the disclosure need not include the device itself.

Finally, the language used in the specification has been principally selected for readability and instructional purposes, and it may not have been selected to delineate or circumscribe the inventive subject matter. It is therefore intended that the scope of the disclosure be limited not by this detailed description, but rather by any claims that issue on an application based here on. Accordingly, the embodiments of the present disclosure are intended to be illustrative, but not limiting, of the scope of the disclosure, which is set forth in the following claims.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A method for examining relevancy of documents, wherein the method comprising:
 extracting a plurality of documents from one or more data sources based on a user request;
 receiving a user input from a user, the user input comprising at least one of user intention information and one or more user-queries;
 generating a first ranking score for each of the plurality of documents through domain specific ranking module by correlating the user intention information with each of the plurality of documents, wherein the first ranking score indicates a relevancy level of each of the plurality of documents with respect to the user intention information, wherein correlating the user intention information with each of the plurality of documents comprises:
 for each of the plurality of documents:
 determining a first sentence from the user intention information and a second sentence from a document from the plurality of documents;
 encoding a first set of tokens corresponding to the first sentence and a second set of tokens corresponding to the second sentence by employing a domain-specific advanced language model,
 wherein the first set of tokens correspond to a first set of words in the first sentence and the second set of tokens correspond to a second set of words in the second sentence;
 generating a first attention matrix corresponding to the first set of words and a second attention matrix corresponding to the second set of words to establish dependency relationship between the first set of words and the second set of words;
 generating semantic representations corresponding to the first sentence and the second sentence by employing mutual attention; and
 finetuning the first set of words and the second set of words by providing the first set of words and the second set of words to a dual branch network to determine a finetuned first sentence and a finetuned second sentence,
 wherein the dual branch network is trained to determine the finetuned first sentence and the finetuned second sentence by minimizing a loss function between the semantic representations corresponding to the first sentence and the second sentence, and
 wherein the first ranking score for the corresponding document is determined by employing at least one similarity measurement technique for the finetuned first sentence and the finetuned second sentence;
 highlighting one or more excerpts in each document while displaying the plurality of documents based on the first ranking score; and
 seeking user feedback corresponding to relevancy of each document based on the first ranking score and the highlighted one or more excerpts to train the domain specific ranking module.

2. The method of claim 1, further comprising:
 generating one or more responses corresponding to the one or more user-queries by using domain-specific advanced language model for question-answer (QA);
 seeking user feedback corresponding to accuracy of the one or more responses with respect to the corresponding one or more user-queries; and
 training the advanced language model for question-answer (QA) based on the user feedback to the accuracy of the one or more responses.

3. The method of claim 1, wherein the user request comprises:

a set of keywords relevant to the plurality of documents; or a plurality of unique IDs pertaining to the plurality of documents.

4. The method of claim 1, wherein highlighting the one or more excerpts in each of the plurality of documents comprises:
highlighting at least one important paragraph in each of the plurality of documents by:
generating a second ranking score for each paragraph in each of the plurality of documents with respect to the user intention information; and
selecting at least one paragraph from each of the plurality of documents with highest ranking score with respect to the user intention information; and
highlighting at least one important sentence in the at least one important paragraph by:
calculating attention weights for the plurality of words in the at least one important paragraph and the user intention information;
assigning a score to each of the plurality of words; and
by obtaining a start point and an end point from the at least one important paragraph based on the maximum score.

5. The method of claim 1, wherein the plurality of documents is displayed in an ascending order or a descending order of the first ranking score of each of the plurality of documents.

6. A system for examining relevancy of documents, wherein the system comprises:
a hardware processor configured to:
extract a plurality of documents from one or more data sources based on a user request;
receive a user input from a user, the user input comprising at least one of user intention information and one or more user-queries;
generate a first ranking score corresponding to the plurality of documents through domain specific ranking module by correlating the user intention information with each of the plurality of documents,
wherein each ranking score indicates relevancy level of a document with respect to the user intention information,
wherein to correlate the user intention information with each of the plurality of documents, the processor is configured to:
for each of the plurality of documents:
determine a first sentence from the user intention information and a second sentence from a document from the plurality of documents;
encode a first set of tokens corresponding to the first sentence and a second set of tokens corresponding to the second sentence by employing a domain-specific advanced language model,
wherein the first set of tokens correspond to a first set of words in the first sentence and the second set tokens correspond to a second set of words in the second sentence;
generate a first attention matrix corresponding to the first set of words and a second attention matrix corresponding to the second set of words to establish dependency relationship between the first set of words and the second set of words;
generate semantic representations corresponding to the first sentence and the second sentence by employing mutual attention;
finetune the first set of words and the second set of words by providing the first set of words and the second set of words to a dual branch network to determine a finetuned first sentence and a finetuned second sentence,
wherein the dual branch network is trained to determine the finetuned first sentence and the finetuned second sentence by minimizing a loss function between the semantic representations corresponding to the first sentence and the second sentence, and
wherein the first ranking score for the corresponding document is determined by employing at least one similarity measurement technique for the finetuned first sentence and the finetuned second sentence;
highlight one or more excerpts in each document while displaying the plurality of documents based on the first ranking score;
seek user feedback corresponding to relevancy of each document based on the first ranking score and the highlighted one or more excerpts; and
train the domain specific ranking module based on the user feedback.

7. The system of claim 6, the processor is further configured to:
generate one or more responses corresponding to the one or more user-queries by using domain-specific advanced language model for question-answer (QA);
seek user feedback corresponding to accuracy of the one or more responses with respect to the corresponding one or more user-queries; and
train the advanced language model for question-answer (QA) based on the user feedback on the accuracy of the one or more responses.

8. The system of claim 6, wherein the user request comprises:
a set of keywords relevant to the plurality of documents; or
a plurality of unique IDs pertaining to the plurality of documents.

9. The system of claim 6, wherein to highlight the one or more excerpts in each of the plurality of documents, the processor is further configured to:
highlight at least one important paragraph in each of the plurality of documents by:
generating a second ranking score for each paragraph in each of the plurality of documents with respect to the user intention information; and
selecting at least one paragraph from each of the plurality of documents with highest ranking score with respect to the user intention information; and
highlight at least one important sentence in the at least one important paragraph by:
calculating attention weights for a plurality of words in the at least one important paragraph and the user intention information;
assigning a score to each of the plurality of words; and
obtaining a start point and an end point from the at least one important paragraph based on the score.

10. A non-transitory computer-readable medium storing computer-executable instructions for examining relevancy of documents, the stored instructions, when executed by a processor, cause the processor to perform operations comprising:
extracting a plurality of documents from one or more data sources based on a user request;

receiving a user input from a user, the user input comprising at least one of user intention information and one or more user-queries;
generating a first ranking score for each of the plurality of documents through domain specific ranking module by correlating the user intention information with each of the plurality of documents, wherein the first ranking score indicates a relevancy level of each of the plurality of documents with respect to the user intention information, wherein correlating the user intention information with each of the plurality of documents comprises:
for each of the plurality of documents:
determining a first sentence from the user intention information and a second sentence from a document from the plurality of documents;
encoding a first set of tokens corresponding to the first sentence and a second set of tokens corresponding to the second sentence by employing a domain-specific advanced language model,
wherein the first set of tokens correspond to a first set of words in the first sentence and the second set of tokens correspond to a second set of words in the second sentence;
generating a first attention matrix corresponding to the first set of words and a second attention matrix corresponding to the second set of words to establish dependency relationship between the first set of words and the second set of words;
generating semantic representations corresponding to the first sentence and the second sentence by employing mutual attention; and
finetuning the first set of words and the second set of words by providing the first set of words and the second set of words to a dual branch network to determine a finetuned first sentence and a finetuned second sentence,
wherein the dual branch network is trained to determine the finetuned first sentence and the finetuned second sentence by minimizing a loss function between the semantic representations corresponding to the first sentence and the second sentence, and
wherein the first ranking score for the corresponding document is determined by employing at least one similarity measurement technique for the finetuned first sentence and the finetuned second sentence;
highlighting one or more excerpts in each document while displaying the plurality of documents based on the first ranking score; and
seeking user feedback corresponding to relevancy of each document based on the first ranking score and the highlighted one or more excerpts to train the domain specific ranking module.

11. The non-transitory computer-readable medium of claim 10, wherein the processor is further configured to:
generating one or more responses corresponding to the one or more user-queries by using domain-specific advanced language model for question-answer (QA);
seeking user feedback corresponding to accuracy of the one or more responses with respect to the corresponding one or more user-queries; and
training the advanced language model for question-answer (QA) based on the user feedback to the accuracy of the one or more responses.

12. The non-transitory computer-readable medium of claim 10, wherein the user request comprises:
a set of keywords relevant to the plurality of documents; or
a plurality of unique IDs pertaining to the plurality of documents.

13. The non-transitory computer-readable medium of claim 10, wherein the processor is configured to highlight the one or more excerpts in each of the plurality of documents by:
highlighting at least one important paragraph in each of the plurality of documents by:
generating a second ranking score for each paragraph in each of the plurality of documents with respect to the user intention information; and
selecting at least one paragraph from each of the plurality of documents with highest ranking score with respect to the user intention information; and
highlighting at least one important sentence in the at least one important paragraph by:
calculating attention weights for the plurality of words in the at least one important paragraph and the user intention information;
assigning a score to each of the plurality of words; and
by obtaining a start point and an end point from the at least one important paragraph based on the score.

* * * * *